United States Patent
Boyd et al.

(10) Patent No.: US 7,758,500 B2
(45) Date of Patent: Jul. 20, 2010

(54) SOFT TISSUE RETRACTOR AND METHOD FOR PROVIDING SURGICAL ACCESS

(75) Inventors: Stephen W. Boyd, Redwood City, CA (US); James R. Flom, Palo Alto, CA (US)

(73) Assignee: Edwards Lifesciences LLC, Irvine, CA (US)

( * ) Notice: Subject to any disclaimer, the term of this patent is extended or adjusted under 35 U.S.C. 154(b) by 40 days.

(21) Appl. No.: 10/943,195

(22) Filed: Sep. 16, 2004

(65) Prior Publication Data

US 2005/0043592 A1 Feb. 24, 2005

Related U.S. Application Data

(60) Continuation of application No. 09/527,485, filed on Mar. 16, 2000, now Pat. No. 6,814,700, which is a continuation of application No. 09/047,122, filed on Mar. 24, 1998, now Pat. No. 6,142,935, which is a division of application No. 08/610,619, filed on Mar. 4, 1996, now Pat. No. 5,810,721.

(51) Int. Cl.
A61B 1/267 (2006.01)
(52) U.S. Cl. ...................................... 600/206
(58) Field of Classification Search ................. 600/206, 600/212, 223, 245, 233, 199, 236, 241
See application file for complete search history.

(56) References Cited

U.S. PATENT DOCUMENTS

| | | | |
|---|---|---|---|
| 1,810,466 A * | 6/1931 | Deutsch ...................... | 128/887 |
| 2,070,670 A | 2/1937 | Marshall | |
| 2,305,289 A | 12/1942 | Coburg | |
| 2,701,562 A * | 2/1955 | Michael et al. ............. | 600/217 |
| 2,739,587 A | 3/1956 | Scholl | |
| 3,111,943 A | 11/1963 | Orndorff | |
| 3,332,417 A | 7/1967 | Blanford et al. | |
| 3,347,226 A | 10/1967 | Harrower | |
| 3,347,227 A * | 10/1967 | Harrower ..................... | 128/850 |
| 3,397,692 A * | 8/1968 | Creager, Jr. et. al. ........ | 128/850 |
| 3,416,520 A | 12/1968 | Creager, Jr. | |
| 3,473,528 A | 10/1969 | Mishkin et al. | |
| 3,523,534 A | 8/1970 | Nolan | |

(Continued)

FOREIGN PATENT DOCUMENTS

WO WO 97/32514 9/1997

(Continued)

*Primary Examiner*—Cris L Rodriguez
*Assistant Examiner*—Rachel R Steitz
(74) *Attorney, Agent, or Firm*—Michael L. Crapenhoft

(57) ABSTRACT

The present invention provides a retractor for providing surgical access through a passage in tissue, together with methods for its use and deployment. The retractor comprises an anchoring frame having an upper surface, a lower surface, and an opening therethrough which defines an axial axis. A flexible tensioning member is attached to the frame, and is extendable from the frame out of the body through the passage when the frame is positioned through the passage and into a body cavity. This tensioning member is selectively tensionable to spread the tissue radially outwardly from the axial axis. Hence, it is the tension imposed on the flexible liner which effects retraction of the tissue, rather than relying on the structural integrity of an artificial lumen.

12 Claims, 16 Drawing Sheets

U.S. PATENT DOCUMENTS

| | | | |
|---|---|---|---|
| 3,638,644 A | 2/1972 | Reick | |
| 3,641,332 A | 2/1972 | Reick et al. | |
| 3,768,477 A | 10/1973 | Anders et al. | |
| 3,841,332 A | 10/1974 | Treacle | |
| 3,863,639 A | 2/1975 | Kleaveland | |
| 4,155,355 A | 5/1979 | Yamamoto | |
| 4,188,945 A | 2/1980 | Wenander | |
| 4,274,398 A | 6/1981 | Scott, Jr. | |
| 4,387,706 A | 6/1983 | Glass | |
| 4,412,532 A * | 11/1983 | Anthony | 600/206 |
| 4,421,107 A * | 12/1983 | Estes et al. | 600/206 |
| 4,430,991 A * | 2/1984 | Darnell | 600/217 |
| 4,434,791 A | 3/1984 | Darnell | |
| 4,492,229 A | 1/1985 | Grunwald | |
| RE32,021 E * | 11/1985 | Scott, Jr. | 600/217 |
| 4,553,537 A | 11/1985 | Rosenberg | |
| 4,560,832 A | 12/1985 | Wilder et al. | |
| 4,562,832 A * | 1/1986 | Wilder et al. | 600/223 |
| 4,726,356 A | 2/1988 | Santilli et al. | |
| 4,777,943 A | 10/1988 | Chvapil | |
| 4,984,564 A * | 1/1991 | Yuen | 600/207 |
| 5,005,108 A | 4/1991 | Pristash et al. | |
| 5,052,374 A | 10/1991 | Alvarhez-Jacinto | |
| 5,054,906 A * | 10/1991 | Lyons, Jr. | 351/205 |
| 5,159,921 A * | 11/1992 | Hoover | 600/207 |
| 5,213,114 A * | 5/1993 | Bailey, Jr. | 128/849 |
| 5,231,974 A | 8/1993 | Giglio et al. | |
| 5,263,922 A | 11/1993 | Sova et al. | |
| 5,351,680 A | 10/1994 | Jung | |
| 5,366,478 A | 11/1994 | Brinkerhoff et al. | |
| 5,391,156 A * | 2/1995 | Hildwein et al. | 604/174 |
| 5,441,044 A | 8/1995 | Tovey et al. | |
| 5,452,733 A | 9/1995 | Sterman et al. | |
| 5,460,170 A | 10/1995 | Hammerslag | |
| 5,476,510 A | 12/1995 | Eberhardt et al. | |
| 5,520,610 A | 5/1996 | Giglio et al. | |
| 5,520,611 A | 5/1996 | Rao et al. | |
| 5,524,644 A * | 6/1996 | Crook | 128/888 |
| 5,556,417 A * | 9/1996 | Sher | 600/236 |
| 5,571,215 A | 11/1996 | Sterman et al. | |
| 5,582,577 A * | 12/1996 | Lund et al. | 600/204 |
| 5,613,751 A | 3/1997 | Parker et al. | |
| 5,613,937 A | 3/1997 | Garrison et al. | |
| 5,618,096 A | 4/1997 | Parker et al. | |
| 5,649,550 A | 7/1997 | Crook | |
| 5,656,013 A * | 8/1997 | Yoon | 600/207 |
| 5,681,341 A | 10/1997 | Lunsford et al. | |
| 5,785,649 A * | 7/1998 | Fowler, Jr. | 600/233 |
| 5,810,721 A * | 9/1998 | Mueller et al. | 600/206 |
| 5,888,247 A | 3/1999 | Benetti | |
| 5,967,970 A * | 10/1999 | Cowan et al. | 600/207 |
| 6,142,935 A | 11/2000 | Flom et al. | |
| 6,176,824 B1 | 1/2001 | Davis | |
| 6,193,652 B1 | 2/2001 | Berky et al. | |
| 6,241,658 B1 | 6/2001 | Goodrich | |
| 6,254,534 B1 * | 7/2001 | Butler et al. | 600/208 |
| 6,478,728 B1 | 11/2002 | Wright | |
| 6,613,952 B2 * | 9/2003 | Rambo | 602/41 |
| 6,723,044 B2 * | 4/2004 | Pulford et al. | 600/208 |
| 6,814,700 B1 * | 11/2004 | Mueller et al. | 600/206 |
| 7,008,377 B2 * | 3/2006 | Beane et al. | 600/207 |
| 2003/0060685 A1 | 3/2003 | Houser et al. | |
| 2003/0095781 A1 | 5/2003 | Williams | |

FOREIGN PATENT DOCUMENTS

| | | |
|---|---|---|
| WO | WO 99/01696 | 1/1999 |

\* cited by examiner

SOFT TISSUE RETRACTOR AND METHOD FOR PROVIDING SURGICAL ACCESS

CROSS-REFERENCES TO RELATED APPLICATIONS

This application is a continuation of U.S. application Ser. No. 09/527,485, filed on Mar. 16, 2000, now issued as U.S. Pat. No. 6,814,700, which is a continuation of U.S. application Ser. No. 09/047,122, filed on Mar. 24, 1998, now issued as U.S. Pat. No. 6,142,935, which is a divisional of U.S. application Ser. No. 08/610,619, filed on Mar. 4, 1996, now issued as U.S. Pat. No. 5,810,721. The complete disclosures of these related U.S. patent applications are hereby incorporated herein by reference for all purposes.

BACKGROUND OF THE INVENTION

1. Field of the Invention

The present invention relates generally to minimally invasive and less invasive surgical access. More particularly, the present invention provides retractors for soft tissues and methods for their use to provide surgical access into body cavities.

Coronary artery disease remains the leading cause of morbidity and mortality in western societies. Coronary artery disease is manifested in a number of ways. For example, disease of the coronary arteries can lead to insufficient blood flow resulting in the discomfort and risks of angina and ischemia. In severe cases, acute blockage of coronary blood flow can result in myocardial infarction, leading to immediate death or damage to the myocardial tissue.

A number of approaches have been developed for treating coronary artery disease. In less severe cases, it is often sufficient to treat the symptoms with pharmaceuticals and lifestyle modification to lessen the underlying causes of disease. In more severe cases, the coronary blockage can often be treated endovascularly using techniques such as balloon angioplasty, atherectomy, or stents.

In cases where pharmaceutical treatment and/or endovascular approaches have failed or are likely to fail, it is often necessary to perform a coronary artery bypass graft procedure using open surgical techniques. Such techniques require that the patient's sternum be opened and the chest be spread apart to provide access to the heart. A source of arterial blood is then connected to a coronary artery downstream from an occlusion, while the patient's heart is maintained under cardioplegia and circulation is supported by cardiopulmonary bypass. The source of blood may be a vessel taken from elsewhere in the body such as a saphenous vein or radial artery, or an artery in the chest or abdomen such as the left or right internal mammary artery or the gastroepiploic artery. The target coronary artery can be the left anterior descending artery, right coronary artery, circumflex artery, or any other coronary artery which might be narrowed or occluded.

While very effective in many cases, the use of open surgery to perform coronary artery bypass grafting is a highly traumatic to the patient. The procedure requires immediate postoperative care in an intensive care unit, a total period of hospitalization of seven to ten days, and a recovery period that can be as long as six to eight weeks.

Recently, it has been proposed to utilize minimally invasive surgical techniques and procedures to perform coronary artery bypass grafting and other traditionally open-chest cardiac surgical procedures. A wide variety of laparoscopic, arthroscopic, endovascular, and other minimally invasive surgical therapies have been developed. These procedures generally utilize trocars, cannulas, catheters, or other tubular sheaths to provide an artificial lumen, through which specialized tools are inserted and manipulated by the surgeon.

An exemplary minimally invasive bypass method is described in U.S. Pat. No. 5,452,733, assigned to the assignee of the present application, the full disclosure of which is herein incorporated by reference. This exemplary coronary artery bypass method relies on viewing the cardiac region through a thoracoscope and endovascularly portioning the patient's arterial system at a location within the ascending aorta. The bypass procedure is performed under cardiopulmonary bypass and cardioplegia, while the coronary anastomoses are formed within the chest cavity through the use of a plurality of trocar sheaths placed between the patient's ribs.

Although thoracoscopic methods hold great promise for decreasing morbidity and mortality, cost, and recovery time when compared to conventional open surgical coronary bypass procedures, these methods could benefit from still further improvements. In particular, the surgical access provided by known trocar sheaths has not been optimally adapted for performing thoracoscopic coronary artery bypass. The length of conventional trocar sheaths and the small size of their lumens limits the maneuverability of surgical instruments and inhibits the ability to look directly into the chest cavity while an instrument is positioned through the trocar sheath.

It would therefore be desirable to provide improved surgical access devices and methods for their use in performing less invasive coronary artery bypass grafting and other thoracoscopic surgical procedures, and minimally invasive surgical procedures in general. It would be particularly desirable if such devices and techniques provided atraumatic retraction of soft tissue of the chest wall to create the largest possible surgical access window without resorting to a sternotomy or gross retraction or removal of the ribs. Preferably, such improved surgical access devices and methods would provide a flexible access lumen which could be positioned and sized to meet the individual patient's physiology. The devices should have minimum height so as to extend as little as possible from the inner or outer surfaces of the chest wall. It would further be desirable if such access devices and methods allowed direct or magnified viewing of the internal procedure from outside the patient body, thereby decreasing the time and trauma associated with the internal surgical procedure, and increasing overall efficacy over both open surgical procedures and minimally invasive surgical procedures performed through the small trocar sheaths which have been relied on in the prior art.

2. Description of the Background Art

Conventional thoracoscopic techniques are described in Landreneau et al. (1992) *Ann. Thorac. Surg.* 54:800-807. Conventional open surgical procedures for performing coronary artery bypass grafting are described in Kirkland and Barratt Boyes, Cardiac Surgery, John Wiley and Sons, Inc., New York, 1993 (2nd Ed.).

A minimally invasive method for performing coronary artery bypass grafting using an anterior mediastinotomy, including excision of either the third or fourth costal cartilage, was described by Robinson et al. in *J. Card. Surg.* (1995) 10:529-536.

U.S. Pat. No. 5,391,156 describes a flexible endoscopic surgical port having a tubular body, the outer end of which is optionally divisible into a plurality of flaps, thereby matching the length of the tubular body with the thickness of a body wall. A retainer ring engages the flaps to hold the port axially, while the hoop strength of the tubular body holds the adjacent tissue in a retracted position. U.S. Pat. No. 4,274,398 describes a surgical retractor having elastic tubes which hold hooks under radial tension from a notched frame. U.S. Pat. Nos. 4,430,991, and 4,434,791, describe similar surgical retractor frames for use with hooked members. Such a system is commercially available under the trade name LoneStar Retractor System™.

A surgical drape having a central open ring for insertion over known surgical retractors is commercially available from Becton Dickinson of Franklin Lakes, N.J. under the tradename Vidrape®. Relevant minimally invasive methods and devices for heart surgery are described in U.S. Pat. No. 5,452,733; U.S. patent application Ser. No. 08/163,241, filed Dec. 6, 1993; U.S. patent application Ser. No. 08/194,946, filed Feb. 11, 1994; U.S. patent application Ser. No. 08/227,366, filed Apr. 13, 1994; and U.S. patent application Ser. No. 08/486,941, filed Jun. 7, 1995, the full disclosures of which are incorporated herein by reference.

SUMMARY OF THE INVENTION

In a first aspect, the present invention provides a retractor for providing surgical access to a body cavity of a patient through a passage in tissue. The retractor comprises an anchoring frame having an upper surface, a lower surface, and an opening therethrough which defines an axial axis. The anchoring frame is positionable through the passage into the body cavity. A flexible tensioning member is attached to the anchoring frame and extendable from the frame out of the body through the passage. The tensioning member is selectively tensionable to spread the tissue radially outwardly from the axial axis. Hence, it is the tension imposed on the flexible tensioning member which effects retraction of the tissue, rather than relying on the structural integrity of a tubular structure such as a trocar sheath.

Generally, an attachment mechanism on the tensioning member maintains tension so as to retract tissue from the passage. Hence, the tensioning member need only be capable of withstanding and transferring the tension imposed by the attachment mechanism, there being no need for a rigid structure having sufficient hoop strength to maintain the tissue in the retracted position. The resulting surgical access window need not be compromised by any rigid lumen wall or rigid blade-type structure, and the retraction load is distributed atraumatically over a wide area of the tissue by the flexible tensioning member.

Preferably, the anchoring frame will have a narrow profile configuration for insertion through an incision into the body cavity, and will be expandable to a wide profile configuration once inside the body cavity. The frame may comprise a variety of collapsible and expandable structures, including a ring of resilient material which expands to the large configuration when released. The tensioning member is preferably formed of a plurality of elongate tabs or strips of cloth, tape, cord, or strap material, ideally comprising an absorbent material such as gauze so as to absorb any fluids released by the tissue bordering the passage. Alternatively, an elastomeric or semi-elastomeric sheet or strip may be used.

In another aspect, the present invention provides a retractor for providing surgical access into a chest cavity defined by a plurality of ribs. The ribs are separated by intercostal tissue and an intercostal width. The retractor comprises an anchoring frame which is insertable into the chest cavity through a passage between two ribs, the frame having an opening. A flexible tensioning member extends from at least two opposing sides of the opening in the frame. The tensioning member is able to extend out of the chest cavity through the passage when the frame is within the chest cavity and the opening in the frame is generally aligned with the passage. The tensioning member may be tensioned to spread the intercostal tissue outward toward the two ribs. Such a retractor is particularly well suited for forming an anterior mediastinotomy or small thoracotomy for use in a less invasive coronary artery bypass grafting procedure or other cardiac procedure.

Generally, an attachment mechanism on the tensioning member maintains outward radial tension from outside the patient to hold the intercostal tissue in a retracted position. In some embodiments, the attachment mechanism comprises an adhesive disposed on the tensioning member to facilitate attachment to an outer surface of the patient's chest. Optionally, a surgical film may be adhered to the exterior of the chest surrounding the passage to facilitate adherence of the tensioning member to the chest wall. In alternative embodiments, the attachment mechanism comprises a plurality of clasps or other coupling devices disposed about an outer ring structure which is positioned outside the body cavity.

In yet another aspect, the present invention provides an illuminated retractor for providing surgical access to a body cavity of a patient through a passage in tissue. The retractor comprises an internal anchor having an opening, the anchor being insertable through the passage and into the body cavity. A tissue restraining structure extends proximally from the internal anchor for holding the passage open sufficiently to provide direct visualization of the internal body cavity from outside the patient. Typically, an external anchor is spaced proximally from the internal anchor on the tissue restraining member. An illuminating device is disposed adjacent to the opening in the internal anchor to facilitate visualization of the cavity through the open passage.

In yet another aspect, the present invention provides a tissue retractor system for providing surgical access through an incision in tissue to a body cavity of a patient. The system generally comprises a retractor and a retractor delivery device. Specifically, the retractor comprises an anchoring frame having an opening, wherein the frame is restrainable into a narrow profile to facilitate insertion of the frame into the body cavity. The frame is expandable into a wide profile when inside the body cavity. A flexible tensioning member extends from the frame adjacent to the opening and is selectively tensionable to retract the tissue adjacent the incision, and is adapted to be secured in tension outside the body cavity.

The retractor delivery device comprises a device body having distal and proximal ends, and a pair of inward facing surfaces near the distal end which restrain a frame of the retractor therebetween to a small profile. A handle supports the inward facing surfaces from a proximal end. An actuator may be provided on the handle to effect expansion of the frame within the body cavity.

The present invention also provides a method for retracting tissue to temporarily widen a penetration into a body cavity, the method comprising positioning an anchoring frame against a tissue surface within the body cavity adjacent to the penetration so that an opening in the frame is aligned with the penetration. The frame has a width across the opening which is wider than the penetration. A tissue restraining member extending from the frame out of the body cavity through the penetration is tensioned so as to urge the tissue adjacent the penetration outwardly.

In a further aspect, the present invention provides a method for performing surgery on a patient's heart, the heart being disposed within a chest cavity defined by a plurality of ribs, the ribs being separated by intercostal tissue and an intercostal width. The method comprises inserting an anchoring frame into the chest cavity through an incision between two ribs, wherein the frame has an opening and a width across the opening wider than the intercostal width. Tension is then imposed on a plurality of flexible tabs extending from the frame adjacent to the opening so as to widen the incision. Surgery is then performed on the heart using instruments positioned through the widened incision.

DESCRIPTION OF THE SPECIFIC EMBODIMENTS

The devices and methods of the present invention are suitable for providing access for a variety of surgical procedures within the cavities of the body. Such access is particularly advantageous during minimally invasive and less invasive surgical procedures in which surgical instruments are introduced through an access window provided by the retraction of tissue.

The present retraction methods and devices will find particular use where direct visualization into a body cavity through a percutaneous penetration facilitates the surgical procedure. Alternatively, an endoscope, laparoscope, thoracoscope, or other visualization device may be inserted through such an access window for telescopic or video-based visualization. Additionally, tissues and/or organs may be temporarily extended through the access window to allow external manipulation during therapy. The retraction methods and devices of the present invention will thus find applications in providing surgical access to the pelvis, abdomen, thorax, and other body cavities, to facilitate surgical intervention on the gall bladder, colon, reproductive organs, kidneys, liver, stomach, heart, lungs, and other body structures.

The present invention will find its most immediate application in less-invasive surgery of the heart, particularly in less-invasive coronary artery bypass grafting, less-invasive valve repair and replacement, and other cardiac procedures. Surgical access windows provided by the flexible tensioning member of the retractor of the present invention will easily flex to adapt to the minimally invasive tools used in less invasive bypass procedures, thereby allowing these tools to be manipulated more easily and used at a wider range of angles than could be accommodated by the rigid and semi-rigid trocar sheaths and conventional rigid retractors of the prior art. By utilizing tension in a flexible strap or tab, the intercostal tissue between ribs may be atraumatically retracted as widely as possible without inflicting a gross displacement of the ribs and the resulting patient trauma. However, where greater access is desired and/or required, the retraction methods and devices of the present invention may also be used in combination with the excision of costal cartilage or even a partial sternotomy or small thoracotomy to maximize the size of the open access port.

Figure 1:
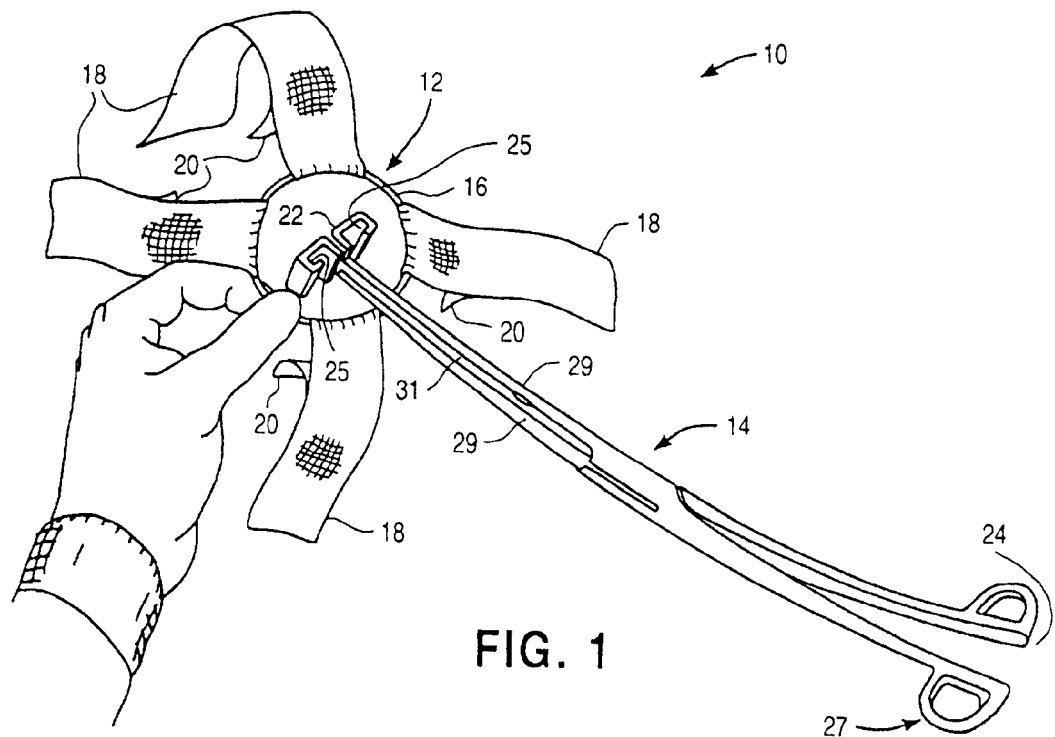
FIG. 1 shows a retractor system according to the principles of the present invention, the system including a retractor and an associated delivery device.

Referring now to FIG. 1, a retraction system 10 comprises a retractor 12 and a delivery device 14. Retractor 12 includes an anchor ring 16 from which a plurality of flexible tabs 18 extend. An adhesive is coated over a portion of each of tabs 18, and a backing strip 20 removably covers the adhesive to facilitate handling the retractor.

Anchoring ring 16 may be either rigid or flexible, but preferably comprises a resilient material biased to form an annular ring shape. A variety of other frame shapes might also be used, including C-shaped, U-shaped, rectangular, elliptical, triangular, parabolic, and optionally including articulated or living hinge joints. In any event, the anchoring frame will have at least two sections separated by an opening or gap such that the frame may be placed through a passage in a body wall into a body cavity and the two sections positioned on either side of the passage with the opening therebetween aligned with the passage. The anchoring ring may optionally be made of a relatively high strength polymer such as Delrin™, nylon, high density polyethylene, and the like. Preferably, the anchoring ring comprises a high strength biocompatible alloy, ideally being a superelastic alloy such as Nitinol®. Such an alloy ring may be formed by welding, crimping the joint with a stainless steel tube, butt jointing with heat shrink tubing, or the like, the ring preferably having a diameter between about 10 mm and 9 cm. The exemplary annular superelastic alloy anchoring ring may be readily compressed to a small configuration for insertion, will readily expand to the large open configuration shown in FIGS. 1-2 once inside the body cavity, and will withstand the compressive loads imposed by flexible tabs 18 during retraction of tissue as described hereinbelow.

The axial dimension of anchoring ring 16 is preferably minimized to provide maximum open working area within the body cavity and to provide maximum maneuverability of instruments positioned through it. In an exemplary embodiment, the anchoring ring has an axial thickness of less than about 20 mm, and preferably less than about 10 mm.

Flexible tabs 18 preferably comprise elongate strips of an absorbent material such as gauze, cloth tape, or the like. Such gauze tabs may be easily looped over anchoring ring 16 and sutured, sewn, adhesively bonded, heat sealed, or welded to themselves. Alternatively, tabs 18 may be directly adhesively bonded to anchoring ring 16, may be molded into the anchoring ring, or may have the anchoring ring woven into the tab material. Use of an absorbent material allows the flexible tab to absorb blood and other fluids which might otherwise seep from the retracted tissue into the body cavity. Where absorbency is less important, flexible tabs 18 may be an elastomer or a flexible, deformable or resilient metal.

The adhesive behind backing strips 20 will generally comprise a medical grade adhesive suitable for attachment to human skin or to paper, cloth, metal or plastic surfaces, such as an acrylate or other suitable adhesive. Conveniently, attachment may be facilitated by the use of a plastic film adhered to the patient's chest prior to insertion of the retractor, allowing backing strips 20 to be affixed securely to the plastic film.

Delivery device 14 generally includes a distal end 22 and a proximal end 24. The distal end includes inward facing surfaces 25 which releasably restrain the anchoring ring in a small profile configuration, while the proximal end 24 includes a handle 27 for manipulation of these inward facing surfaces. Handle 27 comprises a pair of finger loops which may be actuated by passing the thumb and a finger therethrough and separating and/or bringing together the thumb and finger. Arms 29 extend distally to support each of the inward facing surfaces, the arms being hinged to form jaws 31 which widen or narrow the distance between inward facing surfaces 25 as handle 27 is actuated. Preferably, arms 29 are generally U-shaped as shown, extending distally, turning outward, and returning proximally to inward facing surfaces 25. Optionally, a releasable detent or ratchet (not shown) between the handles helps restrain inward facing surfaces 25 at their closest proximity.

Figure 2:
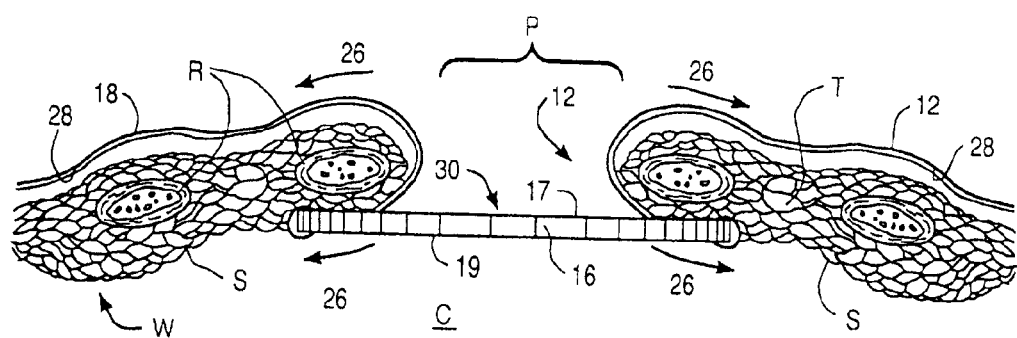
FIG. 2 is a cutaway view of the retractor of FIG. 1 as used for retracting intercostal tissue from between ribs to provide access to the chest cavity.

A particularly advantageous use of the retractor of FIG. 1 for accessing the chest cavity by retracting the soft intercostal tissue between ribs will be described with reference to FIG. 2. A chest wall W is defined by a plurality of ribs R separated by intercostal tissue T. Anchoring ring 16 of retractor 12 is shown inserted through a passage P through the chest wall. As used herein, a passage means any opening, puncture, wound or incision through tissue to a body cavity, whether open or closed. Hence, passage P may comprise an incision, a mediastinotomy, thoracotomy, or other opening formed by the cutting or removal of tissue, bone, or cartilage, a percutaneous opening through tissue, or the like. In any event, tabs 18 extend from the anchoring ring 16 outward through passage P. An upper surface 17 of anchoring ring 16 is placed against an inner surface S of chest wall W, while a lower surface 19 is oriented into the chest cavity C.

As tabs 18 are highly flexible and formed from separate elongate strips, they retract little or no tissue from the passage P when loose. However, when tension is applied to tabs 18, that tension is transmitted along the tab to act in a radial outward direction 26 against the tissue which borders the passage P. The transmission of tension through the flexible tabs results in a retraction of tissue from both outside and inside the body cavity, without interrupting the passage with a rigid trocar sleeve or other rigid retracting structure. Adhesive 28 disposed on tabs 18 conveniently allows the tissue to be held in the retracted position by affixing the tabs to the surface of the chest or to another external structure.

Access to the interior of body cavity C is thus provided through the passage P by retracting tissue so as to form an open window. Tabs 18 are radially opposed, so that opposing radial tensions 26 help to hold anchoring ring 16 in alignment with the open window, and also so that tissue is retracted in opposite directions. Thus, access to the body cavity is provided through an opening 30 in anchoring ring 16, which is preferably larger than the open passage to prevent any interference, and preferably wider than an intercostal width between adjacent, unretracted ribs.

Figure 2A:
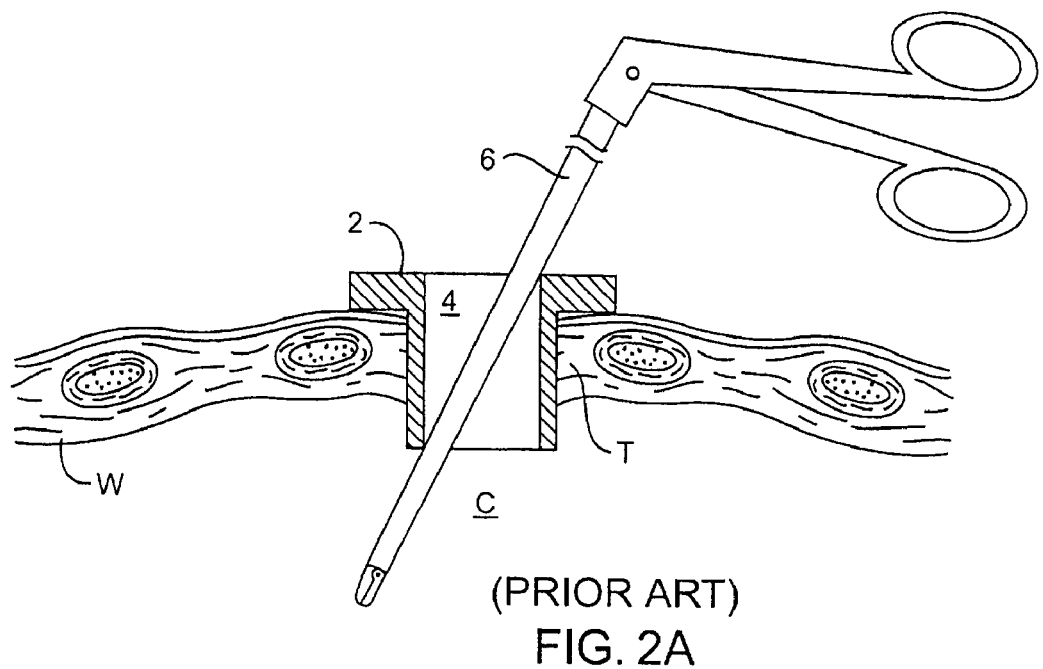
FIG. 2A is a cutaway view of a surgical instrument positioned through a typical known trocar sheath.
Figure 2B:
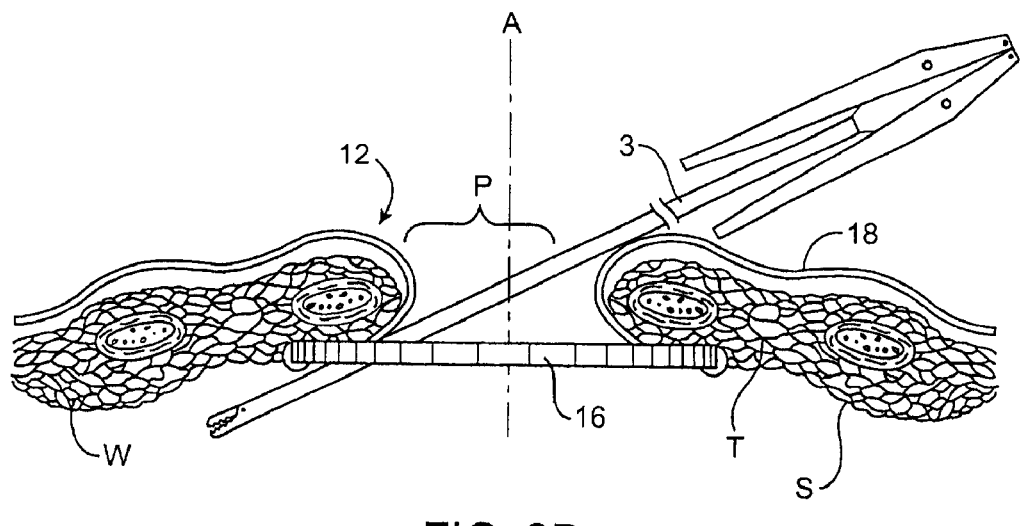
FIG. 2B is a cutaway view of a surgical instrument positioned through the retractor of FIG. 1, showing the increased angulation and maneuverability provided by the surgical access of the present invention.
Figure 3:
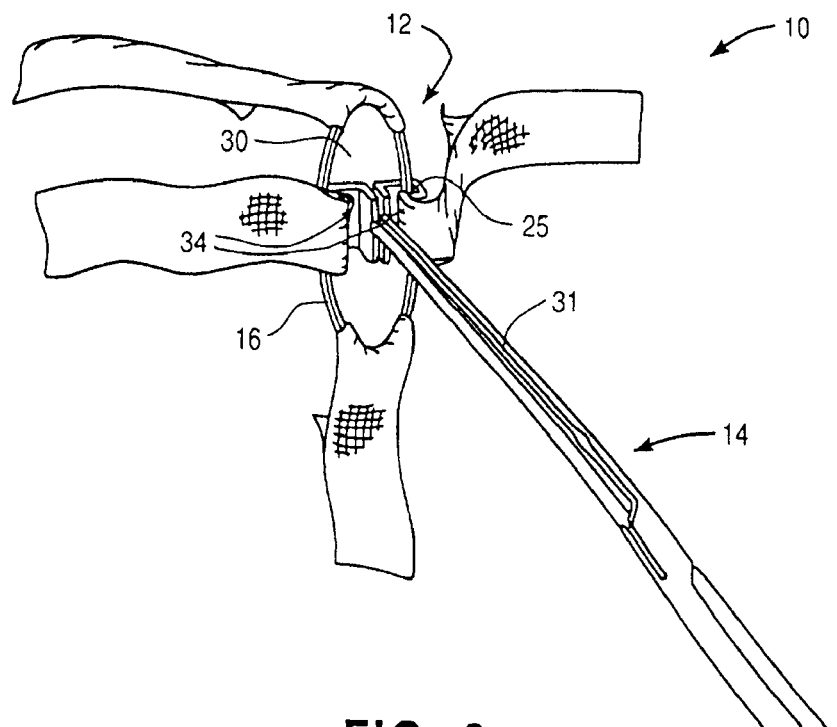
FIG. 3 shows the retractor system of FIG. 1 with the retractor restrained in a small configuration by the delivery device.

The improved access and visualization provided by the retractor of the present invention is seen most clearly in FIGS. 2A and 2B. Known trocar sheath 2 has a structural lumen 4 which must have walls of sufficient rigidity and thickness to retract intercostal tissue T. The length of lumen 4 is significantly greater than the thickness of chest wall W to ensure that the lumen remains open when trocar sheath 2 is canted by a moderately angled surgical tool 6. The length of lumen 4 will also often be increased to allow trocar sheath 2 to accommodate chest walls of varying thickness, further decreasing unimpeded angulation and maneuverability of surgical tool 6. Clearly, direct visualization of an internal procedure through lumen 4 of trocar sheath 2 would be highly problematic, even where surgical tool 6 is limited to the moderate angle shown.

In contrast to known trocar sheaths, retractor 12 provides a surgical access window that accommodates less invasive surgical implement 3 at a large angle relative to axial axis A, and with improved maneuverability and visualization. Tension in tabs 18 retracts intercostal tissue T from passage P, and also pulls anchoring ring 16 firmly against the inner surface S of chest wall W. Not only does this avoid interference from the ring frame, but the tension of tabs 18 will actually compress the thickness of chest wall W adjacent passage P, further increasing the range of motion of implement 3. Finally, if even higher angles are required, the surgeon need only apply the force necessary to locally displace the tissue adjacent the angled tool, as the flexible tabs do not have a structural lumen which resists distortion. It can also be seen in FIG. 2B that visibility through a surgical access window provided by retractor 12 is substantially enhanced, particularly from viewpoints which are at a substantial angle from axial axis A of anchoring ring 16.

Figure 4:
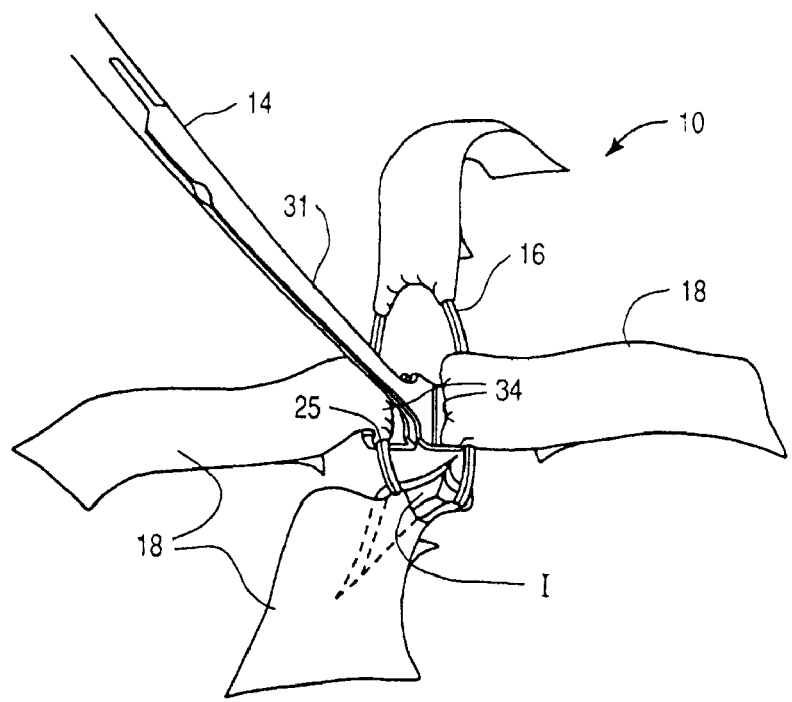
FIGS. 4-6 illustrate a method of using the retractor system of FIG. 1 to provide surgical access to a body cavity.

The deployment of retractor 12 using delivery device 14, will be explained with reference to FIGS. 3-6. Preferably, delivery device 14 is inserted through opening 30 and jaws 31 are opened to align channels 34 with ring 26. Ring 26 is positioned within channels 34 adjacent to inward-facing surfaces 25. The handle is then manipulated so that inward facing surfaces 25 engage the anchor ring to squeeze anchor ring 16 into the elongate narrow profile configuration shown in FIGS. 3 and 4. Typically, delivery device 14 will releasably maintain the anchor ring in the narrow profile configuration during positioning. Anchoring ring 16 is then inserted through incision I, preferably in an edgewise orientation as shown in FIG. 4. As used herein, an edgewise orientation means that the axial axis of anchoring ring 16 is at an angle substantially less than 90 relative to, and preferably parallel to, the surface of the body on which incision I is disposed.

Figure 4A:
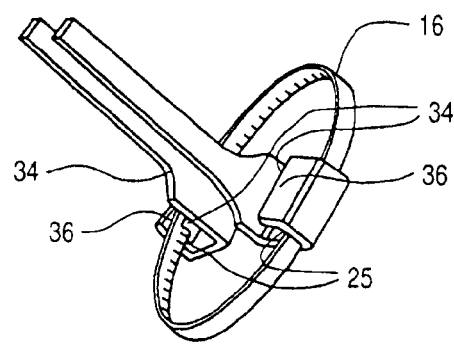
Figure 5:
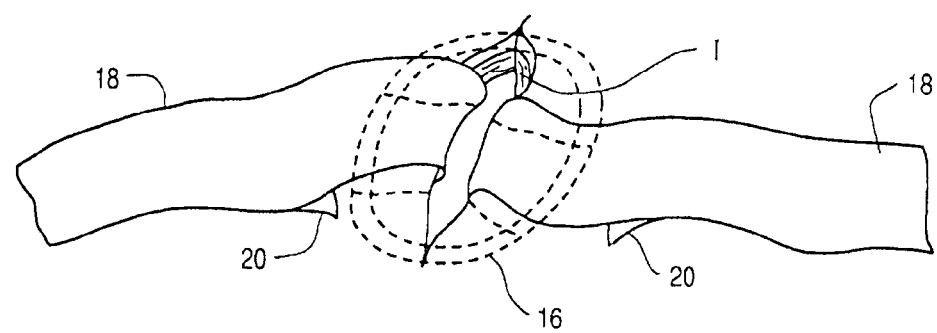

Release of anchor ring 16 within the body cavity is most clearly understood with reference to FIGS. 4A and 5. As shown in FIG. 4A, the anchoring ring may be expanded radially within the body cavity by moving inward-facing surfaces 25 away from one another. The delivery device is withdrawn by first displacing it distally beyond detent 36. Jaws 31 are then closed and the delivery device is withdrawn from incision I.

Figure 6:
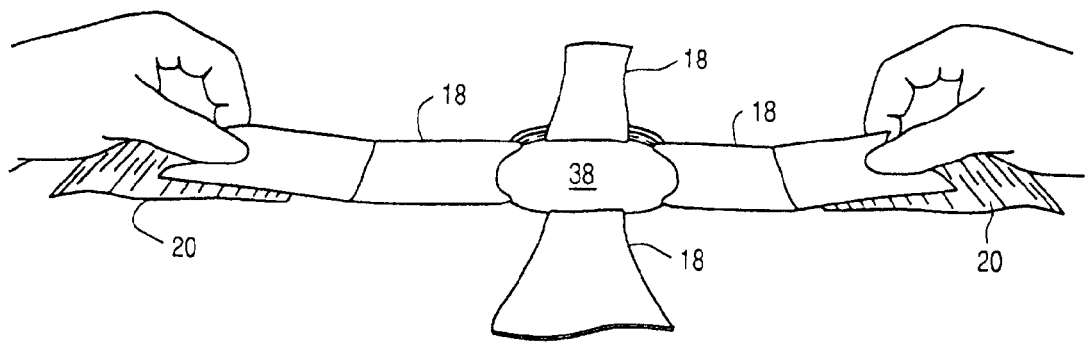

Prior to tensioning, opposed tabs 18 have little effect on the incision I. Conveniently, the tabs may be simply pulled outward by hand to tension tabs 18 and thereby retract the tissue adjacent to the incision. Anchoring ring 16 is drawn into engagement with the interior surface S of the chest wall (as best seen in FIG. 2). When the tissue is sufficiently retracted, backing strips 20 are removed and the tabs affixed in place using the exposed adhesive, as illustrated in FIG. 6. The resulting open window 38 is of maximum size without any significant retraction of the ribs to accommodate various types and sizes of instruments and facilitating a high degree of angulation and motion of such instruments. Furthermore, the chest wall tissue is compressed between the tabs 18 and ring 16, minimizing chest wall thickness to enhance instrument maneuverability. This contrasts with conventional tubular ports, trocar sleeves, and other rigid retractors which have a significant length extending both into and outside of the body cavity, hampering manipulation of instruments.

Figure 6A:
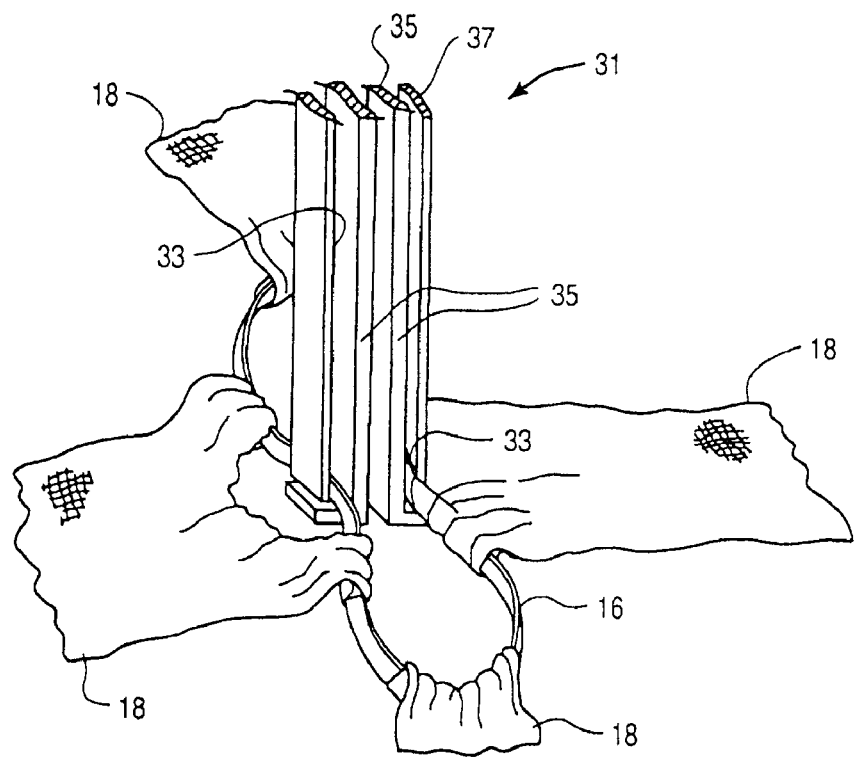
FIGS. 6A-6C illustrate alternative delivery devices for use with the retractor of FIG. 1.
Figure 6B:
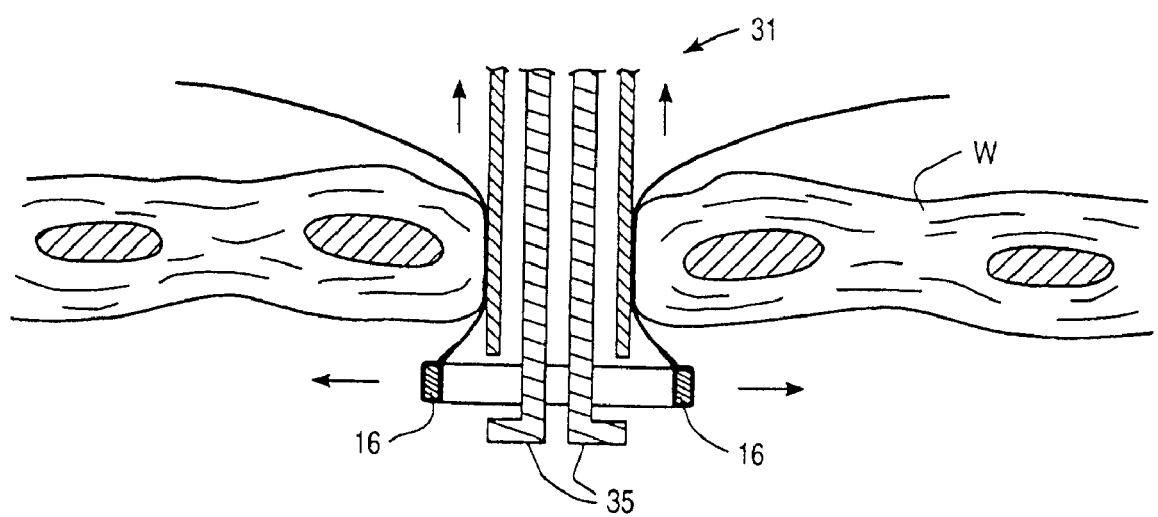

Referring now to FIGS. 6A and 6B, an alternative delivery device 31 includes an inner support member 35 and a slidable outer member 37 having inward facing surfaces 33. Outer member 37 may be retracted proximally relative to an inner support member 35 to allow ring 16 to expand resiliently when released. The inner support member is then withdrawn from the expanded ring. A portion of tab 18 adjacent inward facing surface 33 is removed from FIG. 6A for clarity.

Figure 6C:
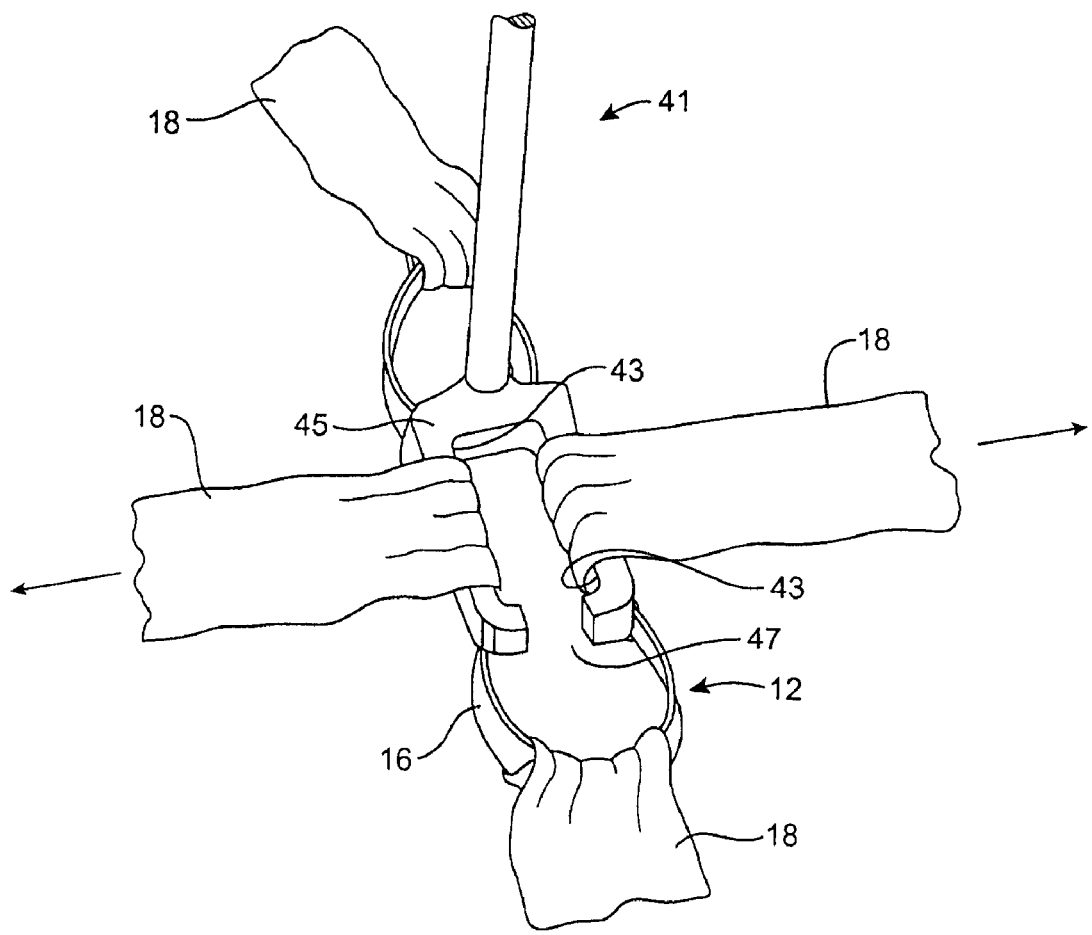
Figure 6G:
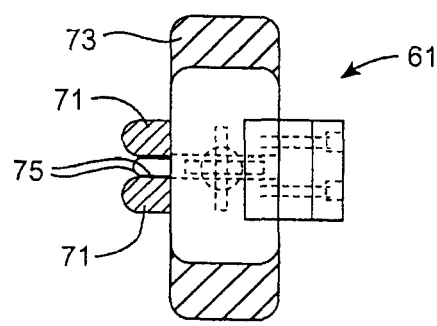
FIGS. 6D-G illustrate an alternative retractor having grommets and an associated delivery device, according to the principles of the present invention.
Figure 6D:
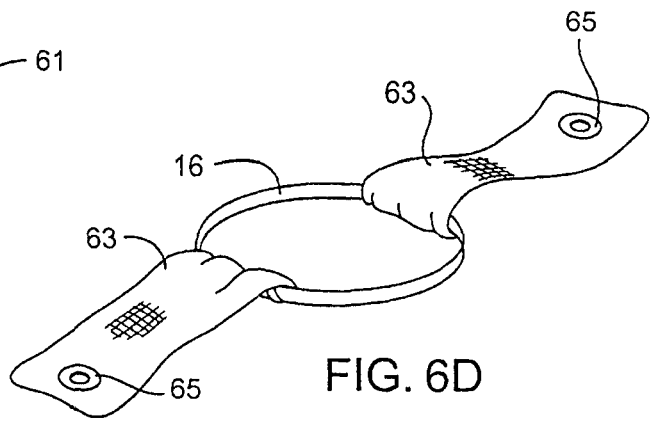
Figure 6F:
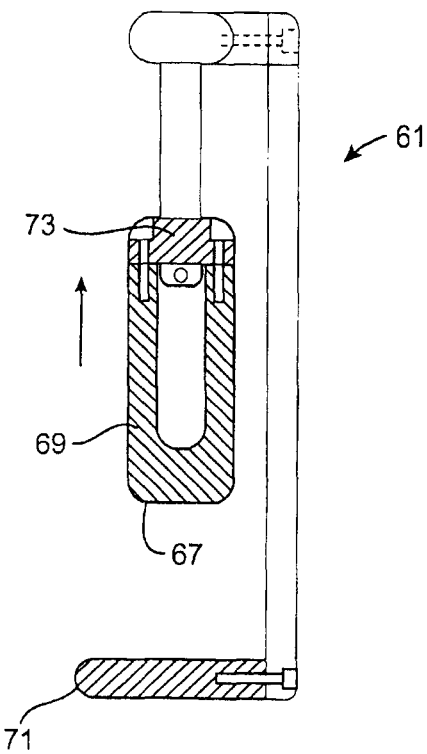
Figure 6E:
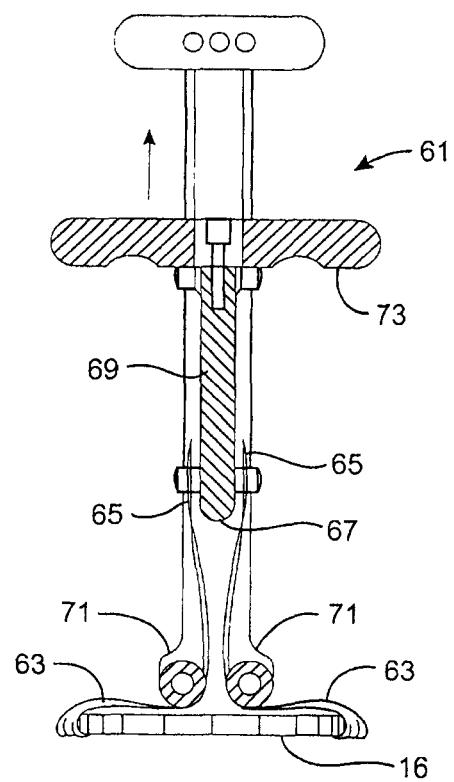

Referring now to FIG. 6C, a still further alternative delivery device 41 includes fixed inward facing surfaces 43 on a distal bracket 45. Fixed surfaces 43 are defined by a slot 47 in bracket 45, the slot accepting a pair of opposing tabs 18. Tensioning of the tabs 18 which pass through slot 47 collapses anchoring ring 16 to the narrow profile configuration during insertion. Releasing the tension from outside the patient allows the anchoring ring 16 to expand resiliently.

A still further alternative delivery device 61 will be described with reference to FIGS. 6D-G. This embodiment makes use of a retractor having tabs 63 with openings which are reinforced with grommets 65. The grommets facilitate holding the tabs with pin 67 of actuator 69. The actuator is upwardly slidable relative to a pair of rollers 71 mounted to a handle 73. Tabs 63 are threaded around rollers 71 and grommets 65 placed over pins 67. As seen most clearly in the front view of FIG. 6F, grasping handle 73 and drawing the actuator in the upward direction indicated will tension the tabs and compress ring 16. Rollers 71 may optionally rotate, or the tabs may slide over the roller's rounded surface. In either case, the distance between the rollers need not change. Hence, the portion of each roller which is adjacent to the other roller defines an inward facing roller surface 75; and the anchoring ring is restrainable in the narrow configuration by these inward facing roller surfaces when the tab is held under tension by pin 67. Alternatively, the grommets maybe disposed on separate tethers attached to the ring, so that the tabs are used only for retraction of tissue.

Figure 7:
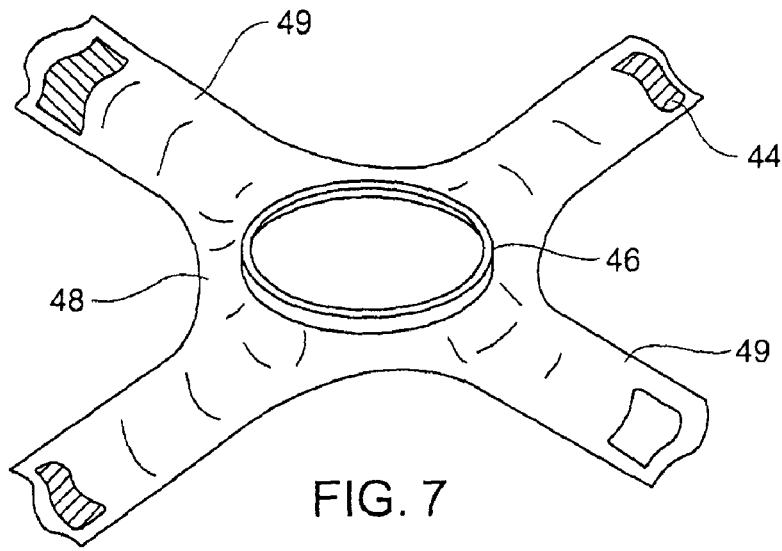
FIGS. 7-9A show alternative embodiments of tissue retractors according to the principles of the present invention.

Referring now to FIG. 7, an alternative embodiment of a retractor according to the principles of the present invention comprises an internal anchoring ring 46 and a tissue restraining member comprising a single-piece sheet 48, which may be flat, bowl-shaped or tubular, preferably comprising a thin semi-elastic polyethylene or urethane material. Adhesive backing 44 disposed on opposed extended tab 49 provides an attachment mechanism to restrain the tissue in the retracted position.

Figure 8:
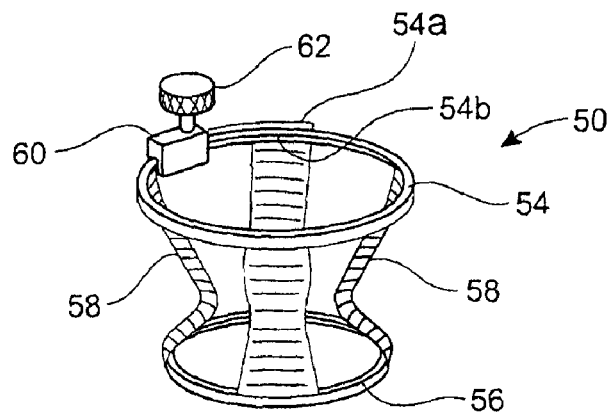

Referring now to FIG. 8, a still further alternative embodiment of the present retractor 50 comprises an outer ring 54, an anchoring ring 56, and tabs 58 coupled therebetween. Expansion mechanism 60 allows the diameter of outer ring 54 to be increased when knob 62 is turned, thereby tensioning tabs 58 when the anchor ring is in position. In an exemplary configuration, outer ring 54 is a split ring with overlapping portions 54a, 54b. Expansion mechanism 60 comprises a clamp for clamping overlapping portions 54a, 54b in position; e.g., knob 62 may be a set screw which engages overlapping portion 54a and urges it against portion 54b. Alternatively, expansion mechanism 60 may mechanically expand ring 54, e.g., by a pinion gear attached to knob 62 which engages a series of teeth along one of overlapping portions 54a, 54b so as to expand ring 54 when the knob is turned.

Figure 9:
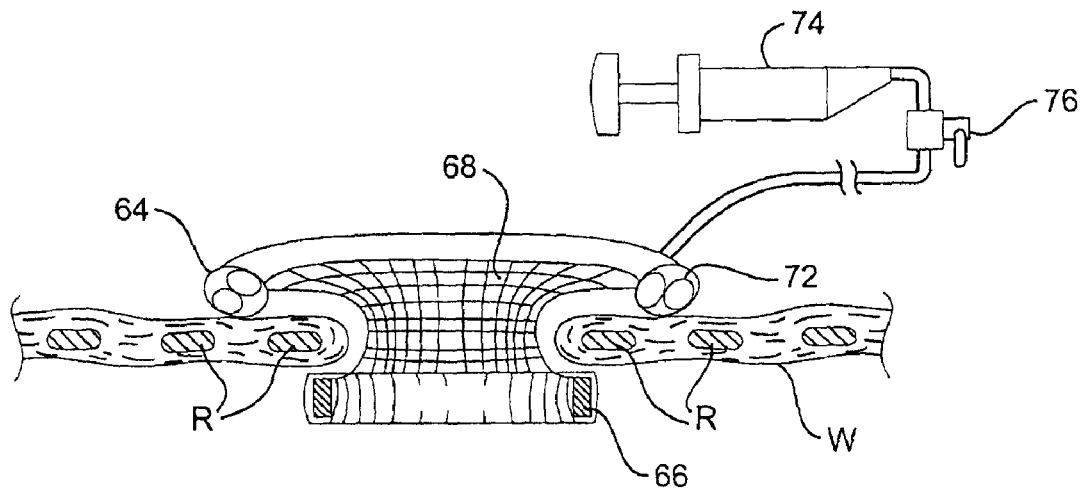

In a further embodiment, shown in FIG. 9, a balloon retractor 60 includes an outer balloon ring 64, an anchor ring 66, and a tubular elastomeric tissue restraining member 68 extending therebetween, as seen retracting tissue in chest wall W. Balloon ring 64 is generally elastomeric or semi-elastomeric, and preferably comprises baffles 72 to give the balloon greater structural integrity and stiffness. The size of the balloon ring (and hence the tension on restraining member 68) may be varied using inflation pump 74 and temporarily fixed with stopcock 76. As the diameter of the balloon ring expands under greater inflation pressure, tab 68 increasingly retracts tissue between ribs R.

Figure 9A:
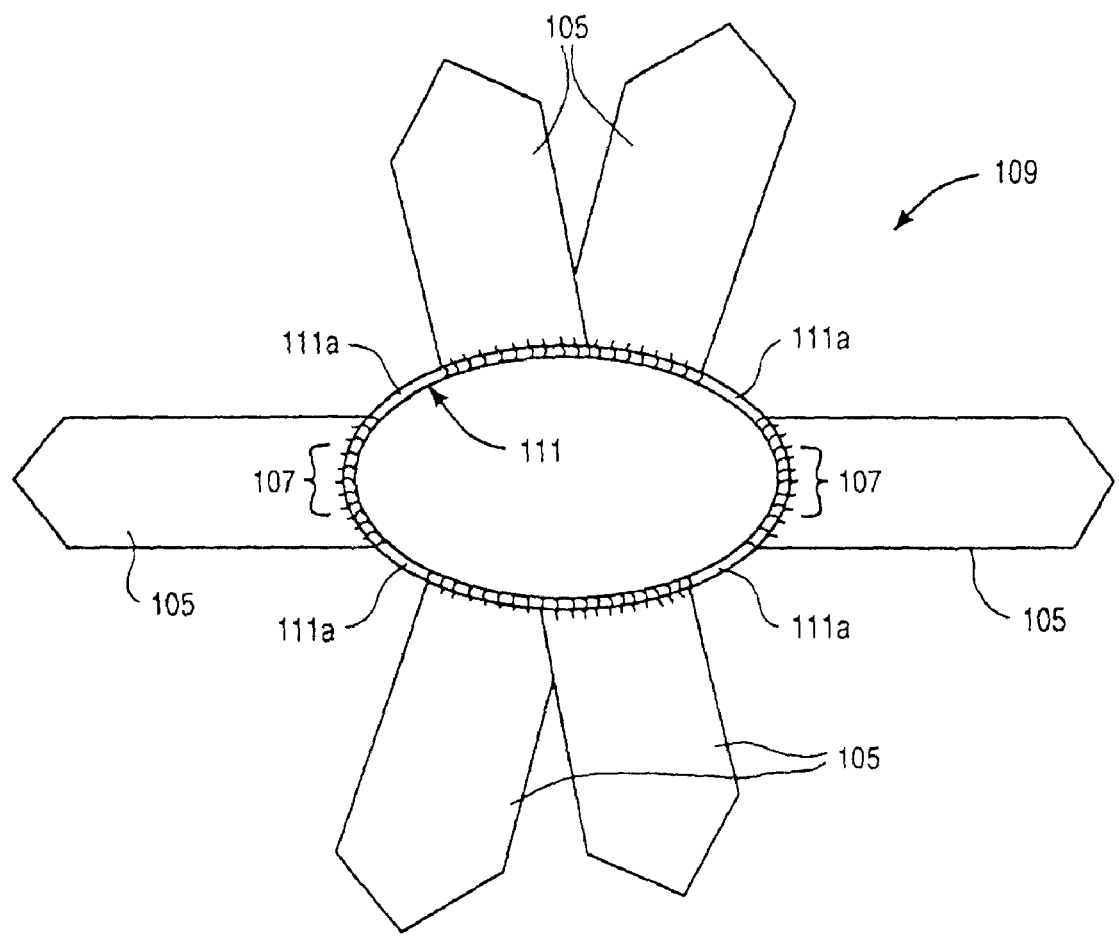

Referring now to FIG. 9A, a still further embodiment of the present retractor 109 includes a polymeric anchoring ring 111 and a plurality of adhesive backed flexible tabs 105. Polymeric anchoring ring 111 includes rigid sections 111A separated by opposed living hinges 107, preferable formed by locally tapering the thickness of the ring material. Optionally, the anchoring ring is machined from nylon, Delrin™, a high density polyethylene, or another relatively high strength polymer. Living hinge 107 facilitates compressing the prosthesis into a narrow diameter configuration by promoting localized bending, and adhesive backed tabs 105 may optionally be attached to the ring by wrapping the tab about the ring so that the tab adhesive adheres to the ring surface. Living hinges 107 may alternatively comprise pin joints or other hinges to provide pivotal motion between sections 111A.

Figure 10A:
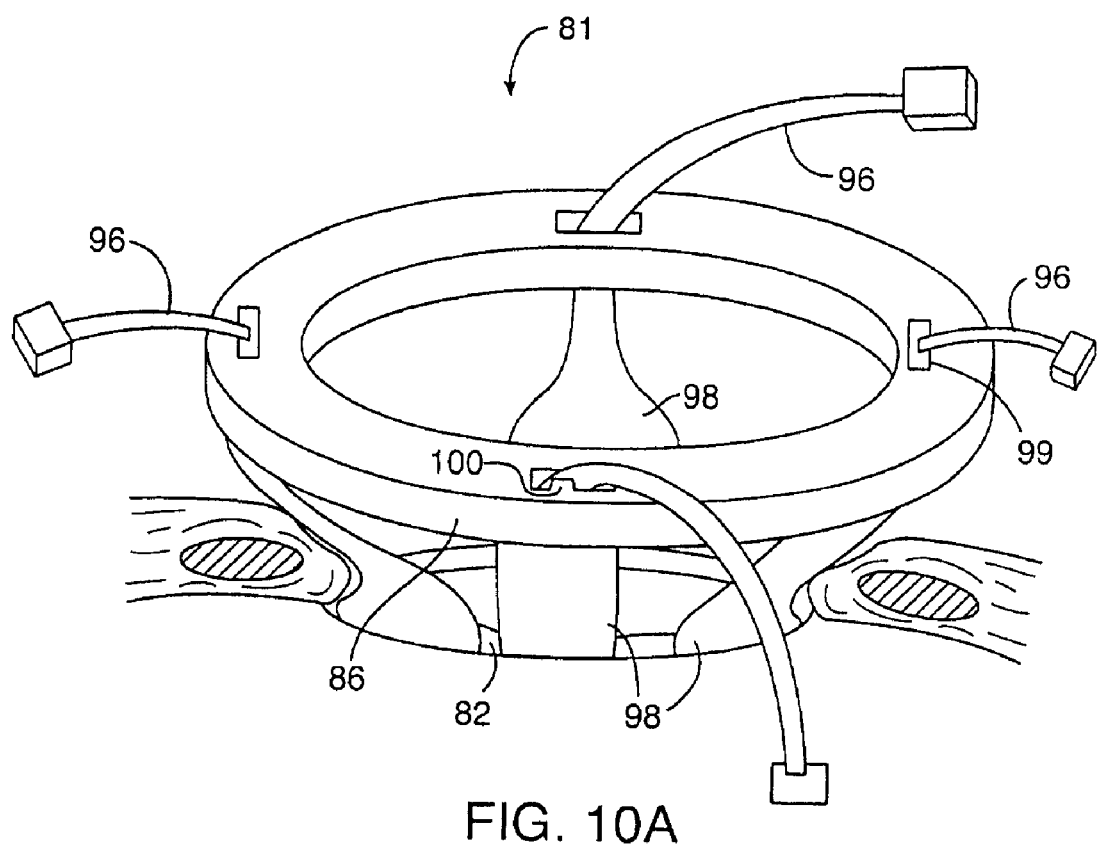
FIGS. 10A-10E illustrate an alternative embodiment of a retractor system according to the principles of the present invention and a method for its use.

Referring now to FIG. 10A, a still further embodiment of the present retractor 81 comprises an anchoring ring 82, tabs 84, and an outer ring 86. Tabs 84 have a tissue restraining portion 98 from which tethers 96 extend. Tethers 96 pass through slots 99 in outer ring 86, the tethers tensioning tissue restraining portions 98 so as to retract tissue from the passage. Conveniently, slots 99 are provided with catches, clamps, or ratchets 100 to engage each tether 96 so as to restrain the tissue in the retracted position. These ratchets facilitate expansion of the access window by manually pulling tethers 96 relative to outer ring 86.

Referring now to FIGS. 10B-10E, a particularly advantageous retractor system 80 comprises retractor 81 and a delivery device including an obturator 88 having a longitudinal channel 89 with inward facing surfaces 90 which restrain the anchor ring therebetween. An actuation handle 92 is located on the proximal portion of the delivery device.

Once the obturator is inserted through the chest wall W, depressing button 94 of handle 92 advances a push rod 95 distally to expel anchor ring 82 distally from the obturator. The individual length of tabs 84 is selected to promote alignment between the anchoring ring opening and the passage through the tissue. Tabs 84 again include a tissue restraining portion 98 from which tethers 96 extend. Tethers 96 initially extend from tabs 84 through slots 99 in outer ring 86, and back to the proximal handle 92 of the delivery device. Thus, proximally retracting obturator 88 relative to the outer ring 86 pulls anchor ring 82 against chest wall W and tensions tethers 96. Tethers 96 are attached to proximal handle 92 by anchors 101 which are held within apertures 103 in proximal handle 92, as shown in FIG. 10D. Rotation of knob 98 of proximal handle 92 releases anchors 101 from apertures 103 to decouple tethers 96 therefrom, allowing the delivery device to be removed from the retractor, leaving an open access port through the retractor as shown in FIG. 10A.

Figure 10F:
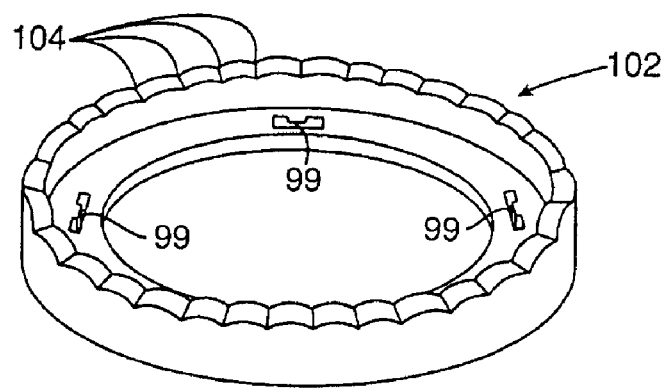
FIG. 10F illustrates an alternative outer ring structure for use with the retractor of FIG. 10A.
Figure 10B:
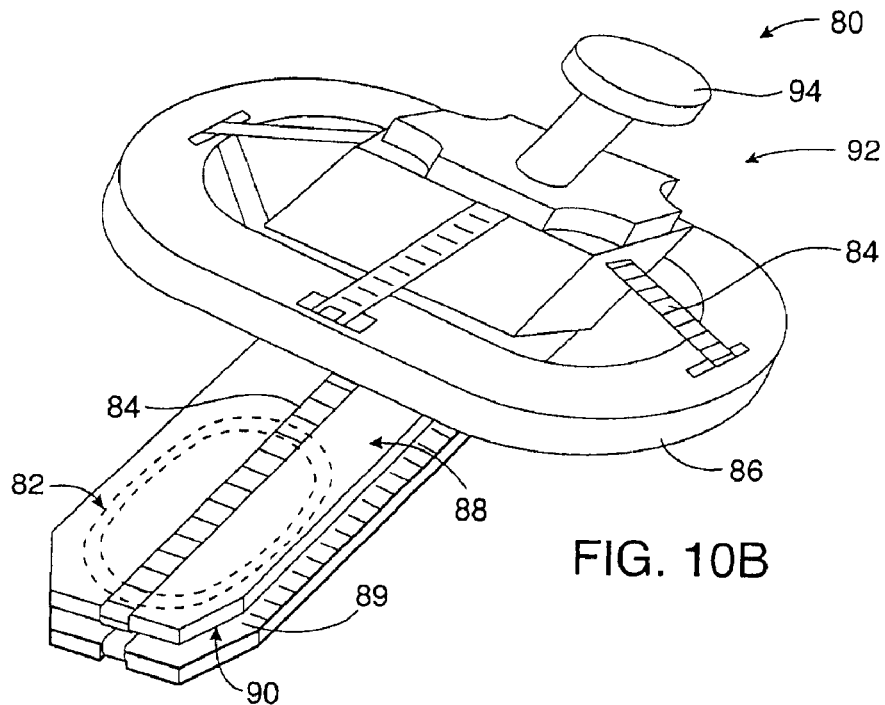
Figure 10C:
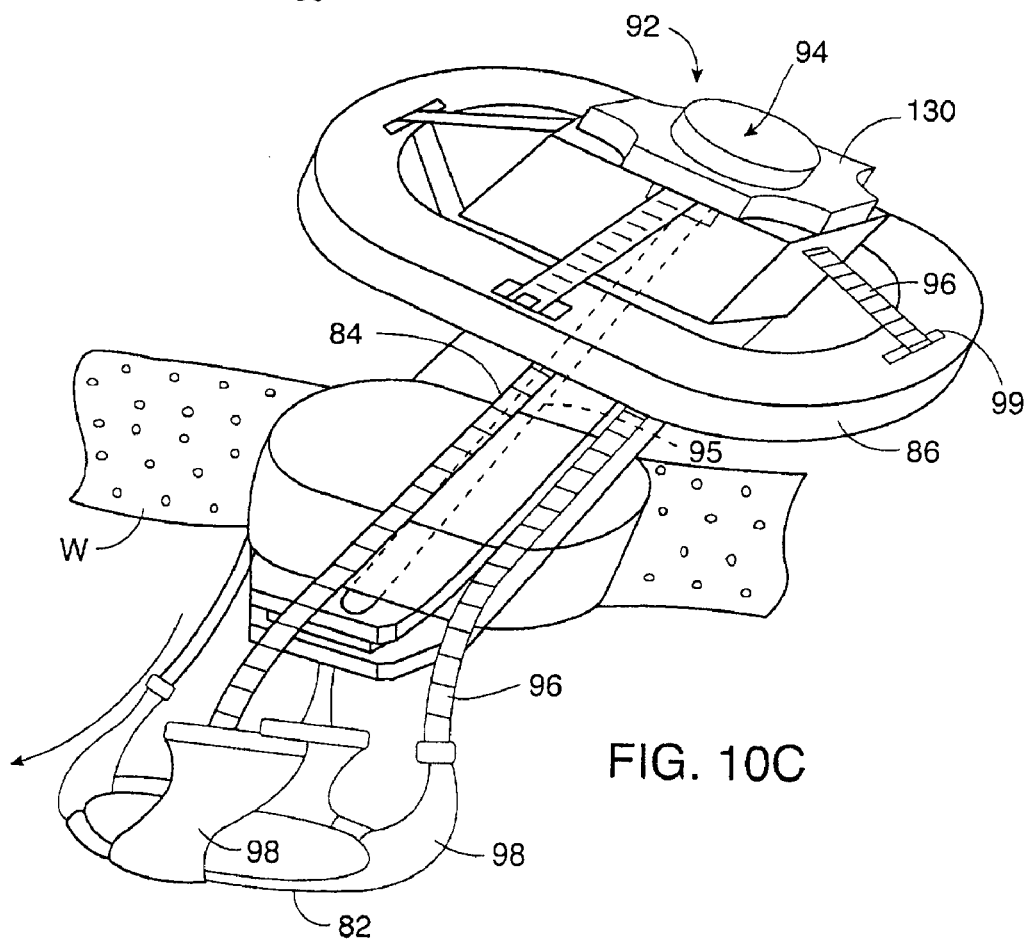
Figure 10D:
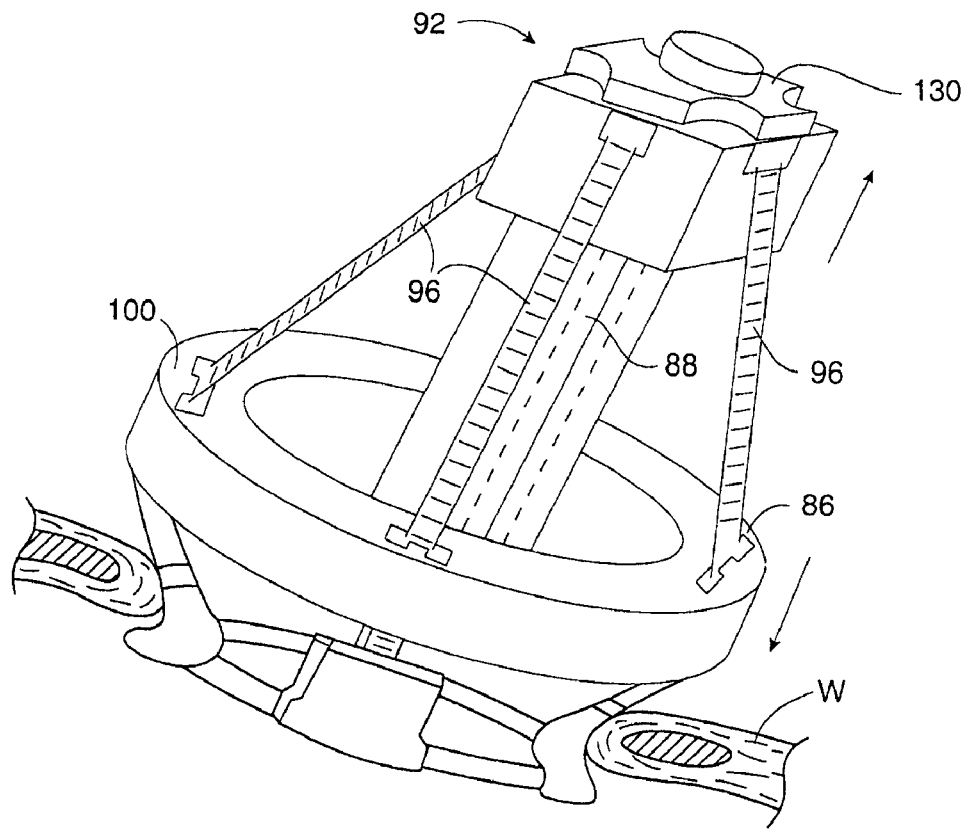
Figure 10E:
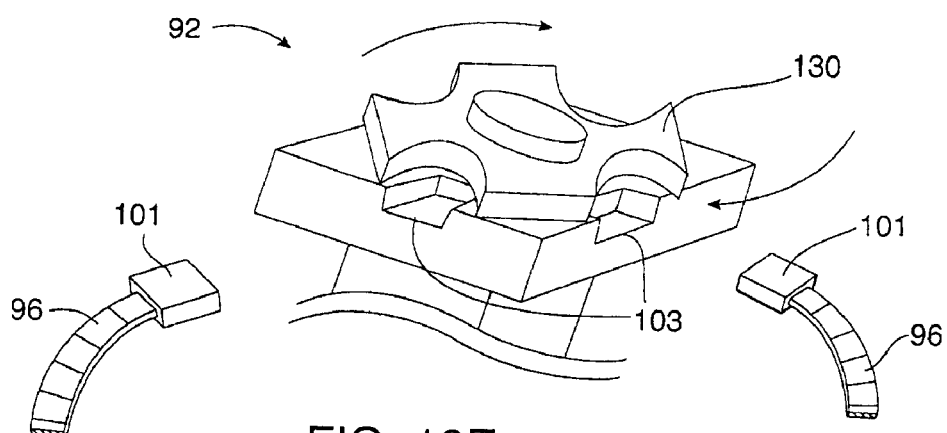

Referring now to FIG. 10F, an alternative outer ring 102 includes a plurality of temporary suture retainers 104 useful in maintaining suture organization in surgical procedures that require a large number of sutures. Retainers 104 may comprise a plurality of radially-oriented slots between 4 and 30 in number configured to frictionally retain a suture thread placed in the slot. Alternatively, retainers 104 may be hooks, eyelets, clamps, cleats, or the like.

Figure 11A:
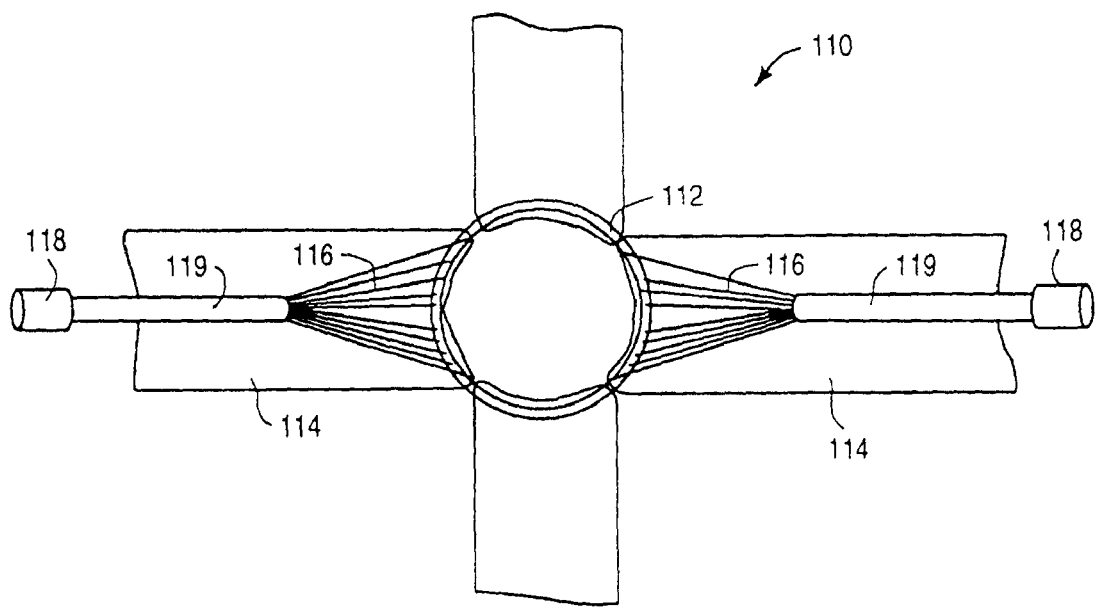
FIGS. 11A and 11B illustrate a retractor having illuminating fiberoptics disposed about an internal anchoring ring to provide both illumination and access to an internal body cavity, according to the principles of the present invention.
Figure 11B:
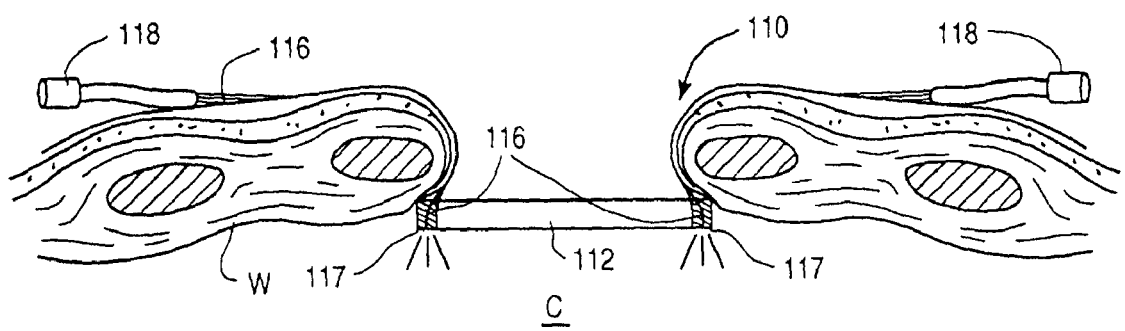

The retractors of the present invention are particularly advantageous when used with direct visualization through an open window, resulting in faster and more cost efficient less invasive surgical procedures. Such direct visualization reduces or avoids the necessity to resort to thoracoscopes and other remote imaging modalities. However, this elimination of the scope from the interior body cavity may also eliminate the primary source of illuminating light, the illumination fiberoptics which are generally provided with such scopes. Therefore, the present invention further provides illuminated retractors, an exemplary embodiment being illustrated in FIGS. 11A and 11B.

Illuminating retractor 110 includes an anchoring ring 112 and a plurality of tabs 114 as described above, and also includes a plurality of illuminating optical fibers 116 disposed about the anchoring ring and having distal ends 117 pointing distally into the body cavity from the lower surface of anchor ring 112. Advantageously, optical fibers 116 extend independently in the proximal direction along the tabs, minimizing any reduction in the size of the opening in the body wall. These independent fibers are then combined together in a cable 119 a short distance from ring 112 and attached to one or more optical couplers 118. Cables 119 may or may not be mounted to one or more tabs 114.

The illuminating ends 117 of optical fibers 116 are generally oriented distally into the body cavity, and may be molded into the anchoring ring, bonded onto an inner or outer surface of the anchoring ring, or may terminate along tabs 114 adjacent to the anchoring ring. Similarly, the dispersed fiberoptics along tabs 114 might be woven into a textile tab, imbedded within a polymer tab with reinforcing or malleable members for optimal light positioning, or be bonded on an inner or outer surface of the tab. Advantageously, the dispersion of the optical fibers across the tab not only minimizes the profile of the fibers, but also helps to maintain the flexibility of the tabs.

Figure 12A:
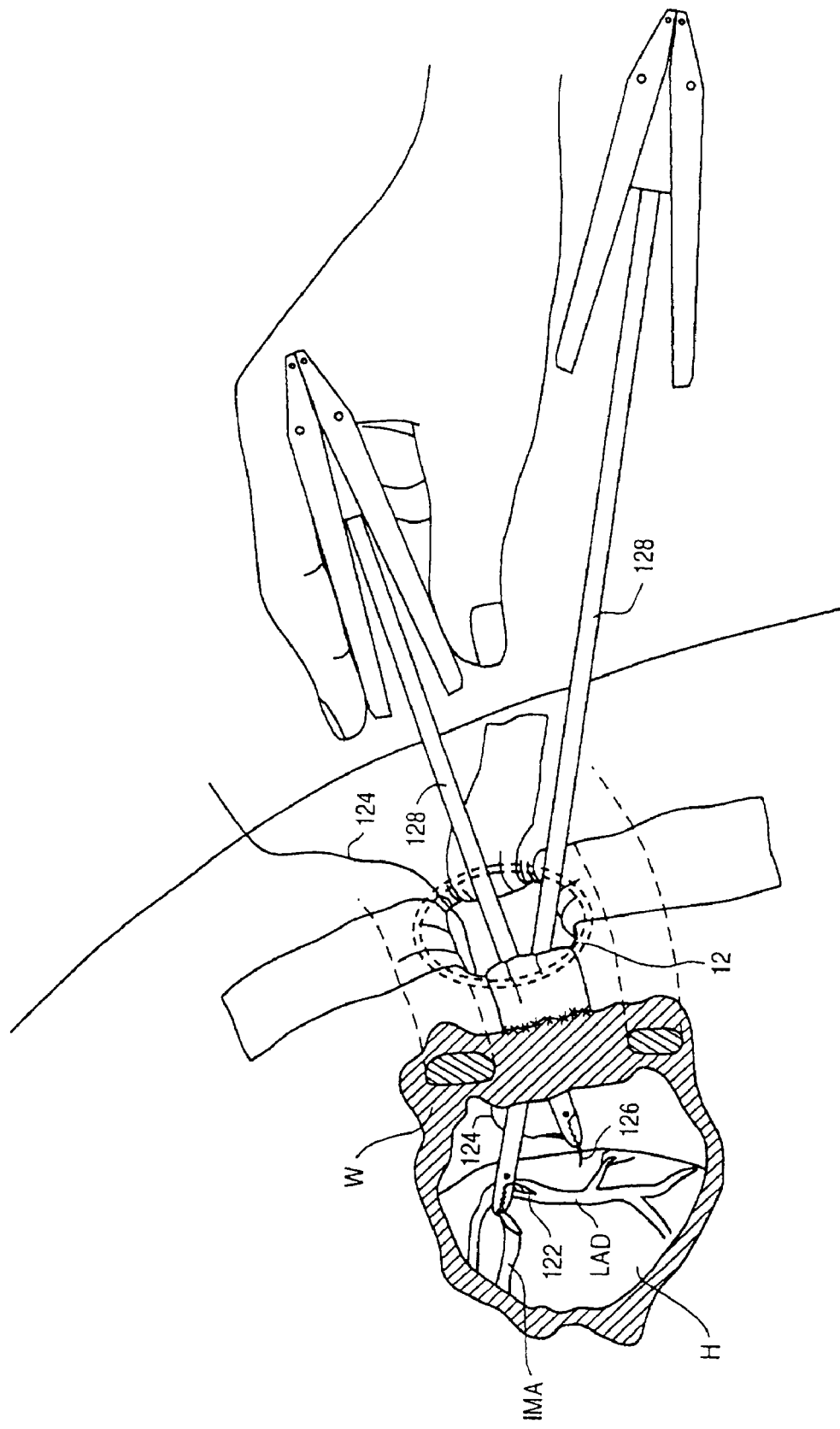
FIGS. 12A and 12B illustrate a method for using the retractor of FIG. 1 for coronary artery bypass grafting, according to the principles of the present invention.
Figure 12B:
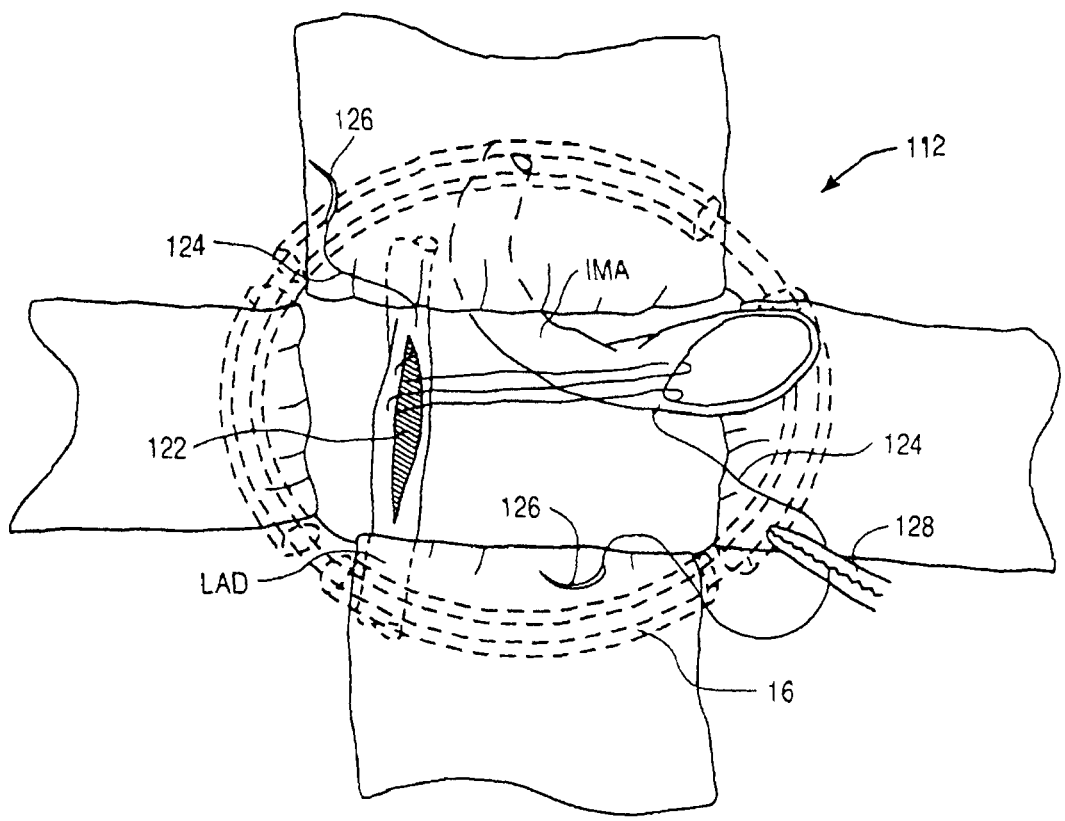

The use of retractor 12 during a coronary artery bypass grafting procedure is illustrated in FIGS. 12A and 12B. As more fully explained in U.S. Pat. No. 5,452,733, previously incorporated herein by reference, an exemplary bypass procedure involves harvesting of the internal mammary artery IMA and joining it with the diseased coronary artery, here the left anterior descending coronary artery LAD. Optionally, a plurality of conventional trocar sheaths, may be used in combination with the retractor 12 of the present invention. Alternatively, the present method for coronary artery bypass grafting may be performed entirely through surgical access windows provided by one or more retractors according to the present invention.

Internal mammary artery IMA may be joined to incision 122 in the coronary artery LAD by a variety of conventional techniques, including suturing, laser welding, tissue gluing, microstapling, and the like. When conventional suturing techniques are used, a length of suture 124 having a needle 126 on at least one end may be manipulated using forceps 128 either inside the chest cavity, or outside the chest cavity directly adjacent retractor 12. In either case, forming the anastomoses is greatly facilitated by the high degree of instrument mobility and by the direct visualization of the procedure provided by retractor 12.

Figure 13:
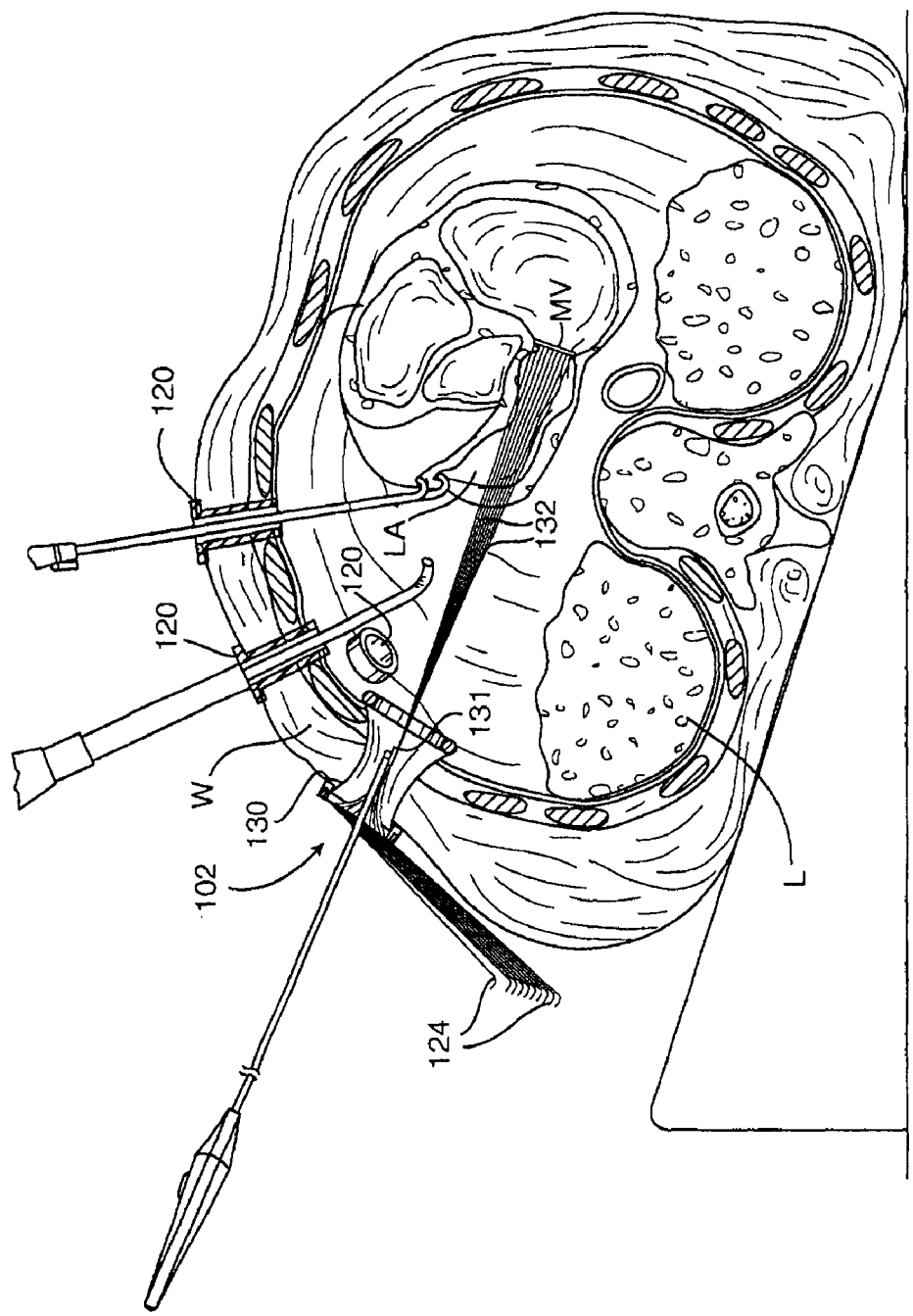
FIG. 13 illustrates a method of retracting tissue during treatment of cardiac valve disease, according to the principles of the present invention.

Referring now to FIG. 13, a retractor 130 similar to the embodiment shown in FIG. 10A and having suture organizing outer ring 102 as illustrated in FIG. 10F is particularly advantageous for use in a less invasive surgical procedure for repair or replacement of a heart valve, for example a mitral valve MV via the left atrium LA. Access to the heart H through the window provided by retractor 130, and/or through trocar sheaths 120 is improved by deflating right lung L. As more fully explained in copending patent application Ser. No. 08/485,600, filed Jun. 7, 1995, the full disclosure of which is incorporated herein by reference, a valve prosthesis 131, such as a mechanical heart valve or annuloplasty ring, may be positioned through retractor 130 into the heart and secured at the native valve position to repair or replace the native valve. A plurality of sutures 132 are used to secure the prosthesis in the heart, and each suture may be drawn out of the chest and retained in suture organizing outer ring 102 as described above in connection with FIG. 10F to prevent tangling and disorganization.

Although the foregoing invention has been described in some detail by way of illustration and example, for purposes of clarity and understanding, certain changes and modifications will be obvious to those with skill in the art. For example, both the outer ring and the anchoring structures may take a variety of forms, including articulated linkages, expandable balloons, multiple layer coils, and the like. Thus, the scope of the present invention is limited solely by the following claims.

What is claimed is:

1. A method for illuminating a body cavity through a passage in tissue, the method comprising:
  surgically creating a passage to a body cavity through tissue of a body;
  inserting a flexible ring having an opening through the passage; and
  retracting the tissue to provide direct visualization of the body cavity through the passage by tensioning at least one flexible tensioning member associated with the flexible ring, wherein retracting the tissue comprises tensioning a plurality of flexible tensioning members associated with the flexible ring, wherein each of the plurality of flexible tensioning members comprises a first end portion and a second end portion, wherein the first end portion of each flexible tensioning member is secured to the flexible ring, wherein retracting the tissue comprises pulling on the second end portion of one or more of the flexible tensioning members, wherein the second end portion done or more of the flexible tensioning members comprises an adhesive, wherein the method further comprises:
  attaching the second end portion to a position outside of the body cavity, wherein such attachment to the position outside of the body cavity comprises adhering the second end portion via the adhesive to the position outside of the body cavity.

2. The method of claim 1, wherein the position outside of the body cavity is a position on the chest of the patient.

3. The method of claim 1, further comprising:
  illuminating the body cavity with an illuminating device disposed at the opening in the flexible ring, wherein the illuminating step comprises illuminating the body cavity with an illuminating device having a plurality of optical fibers with distal ends oriented towards the body cavity.

4. The method of claim 3, further comprising maintaining the plurality of optical fibers independently from each of the plurality of tensioning members.

5. The method of claim 3, further comprising mounting the plurality of optical fibers to one or more of the plurality of tensioning members.

6. A method for retracting tissue to temporarily widen a surgically-formed penetration into a body cavity, the method comprising:

positioning an anchoring ring against a tissue surface within a body cavity;

securing a first end portion at least one flexible tensioning member to the anchoring ring;

selectively tensioning the at least one flexible tensioning member to retract tissue away from the penetration, wherein a second end portion of the flexible tensioning member carries an adhesive, and wherein selectively tensioning the at least one flexible tensioning member comprises attaching the second end portion to a position outside of the body cavity, wherein such attachment to the position outside of the body cavity comprises adhering the second end portion via the adhesive to the position outside of the body cavity.

7. The method of claim 6, further comprising:

illuminating the body cavity by an illuminating device associated with at least one of the anchoring ring and the at least one flexible tensioning member.

8. The method of claim 7, further comprising:

visualizing the body cavity using the illumination of the illuminating device by inserting distal portions of the illuminating device through the surgically-formed penetration.

9. The method of claim 8, further comprising:

integrating distal ends of the illuminating device into one of the anchoring ring and the at least one flexible tensioning member.

10. The method of claim 9, further comprising:

dispersing optic fibers of the illuminating device throughout the at least one flexible tensioning member to minimize the profile of the fibers and to maintain the flexibility of the at least one flexible tensioning member.

11. A method of illuminating a body cavity through a tissue passage, the method comprising:

providing a retractor comprising a flexible internal ring with an opening, a tissue restraining structure having a liner extending from the internal ring at least partially around the opening, an expandable external ring spaced proximally from the internal ring and coupled with the liner, and one or more flexible tensioning members each having a first end secured to the expandable external ring and a second end having an adhesive layer;

creating a tissue passage to a body cavity;

inserting the internal ring through the tissue passage;

retracting the tissue passage open sufficiently to visualize the body cavity from outside the body cavity by tensioning the one or more flexible tensioning members to expand the external ring to tension the liner; and securing the tissue passage in the retracted position by securing the adhesive layer of the one or more flexible tensioning members to a position outside of the body cavity.

12. The method of claim 11, further comprising:

illuminating the body cavity with an illuminating device disposed at the opening of the flexible internal ring.

* * * * *

UNITED STATES PATENT AND TRADEMARK OFFICE
CERTIFICATE OF CORRECTION

| | | |
|---|---|---|
| PATENT NO. | : 7,758,500 B2 | Page 1 of 1 |
| APPLICATION NO. | : 10/943195 | |
| DATED | : July 20, 2010 | |
| INVENTOR(S) | : Boyd et al. | |

It is certified that error appears in the above-identified patent and that said Letters Patent is hereby corrected as shown below:

Col. 12, line 46, should read:

second end portion ~~done~~ <u>of one</u> or more the flexible tension-

Signed and Sealed this
Eighteenth Day of January, 2011

David J. Kappos
*Director of the United States Patent and Trademark Office*